United States Patent [19]

Seele et al.

[11] Patent Number: 5,006,152
[45] Date of Patent: Apr. 9, 1991

[54] AZOLYLMETHYLCYCLOPROPANES AND THEIR USE AS CROP PROTECTION AGENTS

[75] Inventors: Rainer Seele; Reiner Kober, both of Fussgoenheim; Stefan Karbach, Neustadt; Hubert Sauter, Mannheim; Eberhard Ammermann, Ludwigshafen; Gisela Lorenz, Neustadt; Wilhelm Rademacher; Johann Jung, both of Limburgerhof, all of Fed. Rep. of Germany

[73] Assignee: BASF Aktiengesellschaft, Ludwigshafen, Fed. Rep. of Germany

[21] Appl. No.: 409,310

[22] Filed: Sep. 19, 1989

[30] Foreign Application Priority Data

Oct. 10, 1988 [DE]  Fed. Rep. of Germany ....... 3834437

[51] Int. Cl.$^5$ ................ A01N 43/653; C07D 249/08
[52] U.S. Cl. .......................................... 71/92; 71/76; 548/101; 548/262.2; 514/184; 514/383
[58] Field of Search ............................ 548/101, 262.2; 514/184, 383; 71/76, 92

[56] References Cited

U.S. PATENT DOCUMENTS 4,551,469 11/1985 Parry et al. ...................... 514/383
4,670,454 6/1987 Janssen et al. .................... 514/383
4,715,887 12/1987 Kramer et al. .................... 514/383

Primary Examiner—Mary C. Lee
Assistant Examiner—Patricia L. Morris
Attorney, Agent, or Firm—Oblon, Spivak, McClelland, Maier & Neustadt

[57]  ABSTRACT

Azolylmethylcyclopropanes of the formula

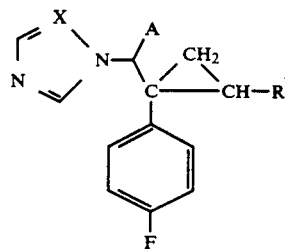

where R is alkyl, cycloalkyl, cycloalkenyl, tetrahydropyranyl, norbornyl, pyridyl, naphthyl, biphenyl or phenyl, and these radicals are substituted or unsubstituted, A is H, F, Cl or Br, and X is CH or N, their plant-tolerated acid addition salts and metal complexes, and fungicides and growth-regulating agents containing these compounds.

16 Claims, No Drawings

AZOLYLMETHYLCYCLOPROPANES AND THEIR USE AS CROP PROTECTION AGENTS

The present invention relates to novel azole compounds, processes for their preparation and fungicides and growth regulators containing these compounds.

It is known that 1-(1,2,4-triazol-1-ylmethyl)-1-(4-fluorophenyl)-2-(2,4-dichlorophenyl)-cyclopropane or 1-(1,2,4-triazol-1-ylmethyl)-1-(4-chlorophenyl)-2-(2-chlorophenyl)-cyclopropane (European Patent No. 121,081) can be used as fungicides. However, the fungicidal actions are unsatisfactory.

We have found that compounds of the formula I

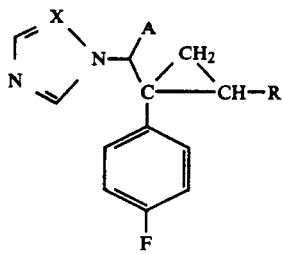

where R is $C_1$–$C_8$-alkyl, $C_3$–$C_8$-cycloalkyl, $C_5$–$C_8$-cycloalkenyl, tetrahydropyranyl, norbornyl, pyridyl, naphthyl, biphenyl or phenyl, and these radicals may be monosubstituted to trisubstituted by halogen, nitro, phenoxy, amino, alkyl, alkoxy or haloalkyl, each of 1 to 4 carbon atoms, A is H, F, Cl or Br and X is CH or N, and their plant-tolerated acid addition salts or metal complexes have a better fungicidal action than known azole compounds and have a good growth-regulating action.

The compounds of the formula I contain chiral centers and are generally obtained in the form of diastereomer mixtures. In the case of the novel compounds, the diastereomers can be separated in a conventional manner, for example on the basis of their different solubilities or by column chromatography, and can be isolated in pure form. Pure enantiomers can be obtained from such an isolated diastereomer by known methods. Both the pure diastereomers or enantiomers and the mixtures of these obtained in the synthesis can be used as active ingredients.

The present invention relates to all these compounds and their mixtures.

R is, for example, methyl, ethyl, isopropyl, n-propyl, n-butyl, sec-butyl, tert-butyl, n-pentyl, neopentyl, hexyl, octyl, trifluoromethyl, trichloromethyl, phenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,3-dichlorophenyl, 2,5-dichlorophenyl, 2,6-dichlorophenyl, 2-chloro-6-fluorophenyl, 2-methoxyphenyl, 3-methoxyphenyl, 4-methoxyphenyl, 2,4-dimethoxyphenyl, 4-ethylphenyl, 4-isopropylphenyl, 4-tert-butylphenyl, 4-tert-butoxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-trifluoromethylphenyl, 3-trifluoromethylphenyl, 4-trifluoromethylphenyl, cyclopropyl, cyclobutyl, cyclopentyl, cyclohexyl, tetrahydropyranyl, 2-cyclohexenyl, 3-cyclohexenyl or norbornyl.

Examples of acid addition salts are the hydrochlorides, bromides, sulfates, nitrates, phosphates, oxalates and dodecylbenzenesulfonates. The activity of the salts is due to the cation, so that the anion is generally unimportant. The novel active ingredient salts are prepared by reacting an azolylmethyloxirane (I) with the acids.

Metal complexes of the active ingredients I or their salts can be formed with, for example, copper, zinc, tin, manganese, iron, cobalt or nickel, by reacting the azolylmethylcyclopropane with corresponding metal salts, for example with copper sulfate, zinc chloride, tin chloride or manganese sulfate.

The compounds of the formula I in which A is H can be prepared, for example, by (a) reacting a compound of the formula II

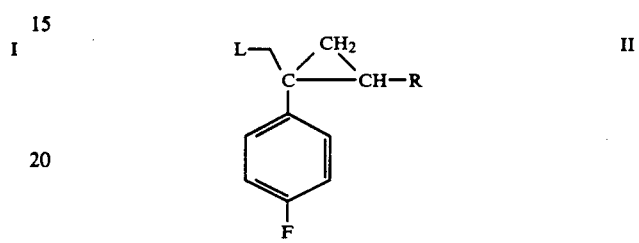

where R has the stated meanings and L is a nucleophilically substitutable leaving group (for example halogen or OH), with a compound of the formula III

where Me is a hydrogen atom, a metal atom (e.g. Na or K) or a trimethylsilyl group and x has the abovementioned meanings, or (b) converting a compound of the formula IV

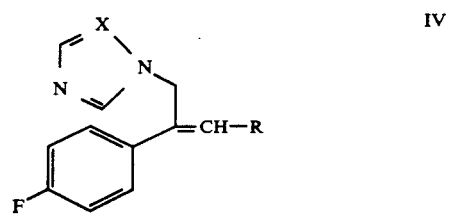

where R and x have the abovementioned meanings, into the cyclopropane.

Where Me is a hydrogen atom, reaction (a) is carried out, for example, in the presence or absence of a solvent or diluent and with or without the addition of an organic or inorganic base and of a reaction accelerator, at from 10° to 120° C. The preferred solvents and diluents include ketones, such as acetone, methyl ethyl ketone and cyclohexanone, nitriles, such as acetonitrile and propionitrile, alcohols, such as methanol, ethanol, isopropanol, n-butanol and glycol, esters, such as ethyl acetate, methyl acetate and butyl acetate, ethers, such as tetrahydrofuran, diethyl ether, dimethoxyethane or dioxane and diisopropyl ether, amides, such as dimethylformamide, dimethylacetamide and N-methylpyrrolidone, and dimethyl sulfoxide, sulfolane and mixtures of these.

Suitable bases, which may also be used as acid acceptors in the reaction, are, for example, alkali metal hydroxides, such as lithium hydroxide, sodium hydroxide and potassium hydroxide, alkali metal carbonates, such as sodium carbonate, potassium carbonate and cesium carbonate, and sodium bicarbonate, potassium bicarbonate, cesium bicarbonate, pyridine and 4-dimethylaminopyridine. However, other conventional bases may also be used.

Preferred reaction accelerators are metal halides, such as sodium iodide or potassium iodide, quaternary ammonium salts, such as tetrabutylammonium chloride, bromide, iodide or bisulfate, or benzyltriethylammonium chloride or bromide, or crown ethers, such as 12-crown-4, 15-crown-5, 18-crown-6 or dibenzo-18-crown-6 or dicyclohexano-18-crown-6.

The reaction is generally carried out at from 10° to 120° C., under atmospheric or superatmospheric pressure, continuously or batchwise.

If Me is a metal atom, reaction (a) is carried out in the presence or absence of a solvent or diluent and with or without the addition of a strong inorganic or organic base, at from −10° to 120° C. The preferred solvents or diluents include amides, such as dimethylformamide, diethylformamide, dimethylacetamide, diethylacetamide, N-methylpyrrolidone or hexamethylphosphorotriamide, and sulfoxides, such as dimethyl sulfoxide, and finally sulfolane.

Suitable bases, which may also be used as acid acceptors in the reaction are, for example, alkali metal hydrides, such as lithium hydride, sodium hydride and potassium hydride, alkali metal amides, such as sodium amide and potassium amide, as well as sodium tert-butoxide, potassium tert-butoxide, triphenylmethyllithium, triphenylmethylsodium, triphenylmethylpotassium, naphthalenelithium, naphthalenesodium or naphthalenepotassium.

Suitable diluents for reaction (b) are polar organic solvents, such as nitriles, e.g. acetonitrile, sulfoxides, e.g. dimethyl sulfoxide, formamides, e.g. dimethylformamide, ketones, e.g. acetone, ethers, e.g. diethyl ether or tetrahydrofuran, and in particular chlorohydrocarbons, e.g. methylene chloride and chloroform.

Reaction (b) is carried out, for example, using a trimethylsulfoxonium salt, e.g. trimethylsulfoxonium iodide, and an alkali, for example an alkali metal alcoholate, e.g. potassium tert-butylate.

The reaction is carried out in general at from 0° to 100° C., preferably from 20° to 80° C. In the presence of a solvent, it is advantageously carried out at the boiling point of the particular solvent.

The compounds of the formula II in which L is a nucleophilically substitutable leaving group can be prepared from the compounds of the formula II (L=OH) by known methods of synthesis, by reaction with halogen carriers, such as hydrogen chloride, hydrogen bromide, thionyl chloride, thionyl bromide, acetyl bromide, phosphorous tribromide, the triphenylphosphine/bromine complex or sulfonyl chlorides, such as methane-, trifluoromethane-, 2,2,2-trifluoroethane-, nonafluorobutane-, 4-methylbenzene-, 4-bromobenzene-, 4-nitrobenzene-, or benzenesulfonyl chloride, in the presence or absence of an inert solvent and of an organic or inorganic base, which may simultaneously be a solvent (cf. for example Houben-Weyl-Müller, Methoden der organischen Chemie, Vol. 5/3 Stuttgart 1964, page 760 et seq.; Vol. 5/4, Stuttgart 1960, page 354 et seq.; Vol. 9, Stuttgart 1955, pages 388 and 633; J. org. Chem. 35 (1970), 3195).

Hydroxycyclopropanes of the formula II (L=OH) are obtained in accordance with the following scheme:

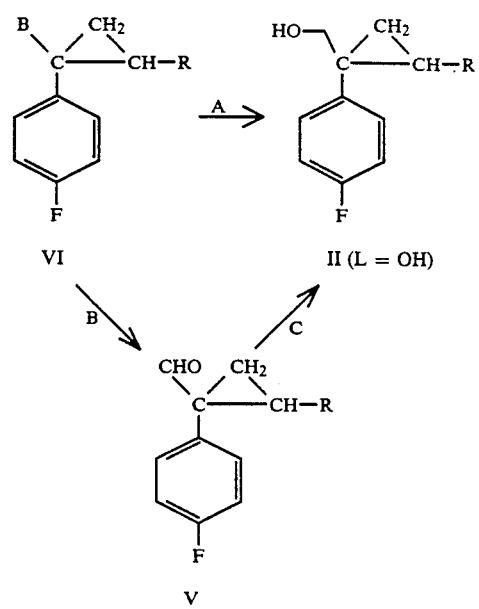

B=CN, COOH, an ester group or an acetalized aldehyde group.

Nitriles of the formula VI (B=CN) can be subjected to solvolysis in an acidic or alkaline medium at from 20° to 120° C. in the presence of a solvent to give the corresponding carboxylic acid derivatives VI (B=COOH), which can be converted into the alcohols II (L=OH) by generally known methods, by reduction with a complex hydride, e.g. lithium aluminum hydride or sodium borohydride, in the case of an anhydride, or with hydrogen in the presence of a catalyst under atmospheric or superatmospheric pressure (process A).

Alternatively, a nitrile VI (B=CN) can be reduced with diisobutylaluminum hydride (cf. E. Winterfeldt, Synthesis 1975, 617) to give the aldehyde V (process B), which is further reduced with a complex hydride, for example sodium borohydride or lithium aluminum hydride, or with hydrogen in the presence of a catalyst to give the alcohol of the formula II (L=OH) (process C).

Cyclopropyl derivatives of the formula VI where R has the abovementioned meanings and B is a nitrile group, an ester group or an unsubstituted or substituted acetalized aldehyde group can preferably be prepared by converting a,β-unsaturated nitriles, carboxylic acid derivatives or aldehyde derivatives of the formula VII

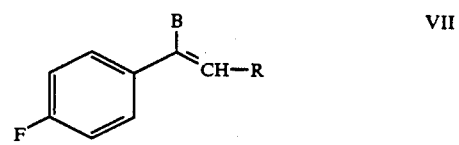

VII where B and R have the abovementioned meanings, into cyclopropane compounds. Particularly suitable for this reaction are trimethylsulfoxonium salts, which are reacted in an inert solvent in the presence of a strong base, for example an alkali metal alcoholate, such as potassium tert-butylate, with a compound of the formula VII, where B and R have the abovementioned meanings (cf. Corey and Chaykovsky, J. Am. Chem. Soc. 64 (1962), 3782).

Further processes for the preparation of substituted cyclopropanes by intramolecular reactions or by reaction of olefins with methylene-carrying reagents, such as diazomethane, or by the Simmon-Smith method are known (cf. for example D. Wendisch in Houben-Weyl-Müller, Methoden der organischen Chemie, Stuttgart 1971, Vol. 4/3, pages 32–148).

The compounds of the formula I in which A is F, Cl or Br can be prepared, for example, by reacting a compound of the formula V

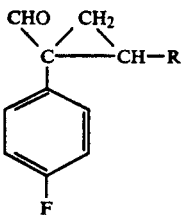

where R has the abovementioned meanings, with a compound of the formula III

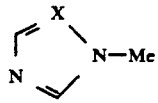

where X and Me have the abovementioned meanings, in the presence of the corresponding thionyl halide. For example, thionyl chloride is used for the preparation of compounds in which A is Cl, and thionyl bromide is used where A is Br.

The reaction is carried out in the presence or absence of a solvent or diluent at from −30° to 80° C. The preferred solvents and diluents include nitriles, such as acetonitrile or propionitrile, ethers, such as tetrahydrofuran, diethyl ether, dimethoxyethane, dioxane or diisopropyl ether, and in particular hydrocarbons and chlorohydrocarbons, such as pentane, hexane, toluene, methylene chloride, chloroform, carbon tetrachloride, dichloroethane or mixtures of these.

The compounds of the formula VII can be prepared by generally known processes for olefin synthesis (Houben-Weyl-Müller, Methoden der organischen Chemie, Georg Thieme Verlag, Stuttgart 1972, Vol. V, 1b).

EXAMPLES

The Examples which follow illustrate the preparation of the active ingredients. I Preparation of the starting materials

EXAMPLE A 52 g of 2-chlorobenzaldehyde are added to a solution of 50 g of 4-fluorophenylacetonitrile in 500 ml of ethanol under a nitrogen atmosphere. The reaction mixture is cooled to 10° C. and 5 g of sodium methylate are added rapidly, the temperature of the solution not exceeding 50° C. The mixture is stirred for one hour at room temperature (20° C.), after which the precipitate formed is filtered off under suction, washed with n-hexane and ethanol and then dried. 91.7 g (96%) of E-1-(4-fluorophenyl)-2-(2-chlorophenyl)-acrylonitrile are obtained.

EXAMPLE B 73.5 g of trimethylsulfonium methylsulfate and 150 ml of 50% strength sodium hydroxide solution are added to a solution of 91.7 g of E-1-(4-fluorophenyl)-2-(2-chlorophenyl)-acrylonitrile in 100 ml of methylene chloride. The reaction mixture is kept at room temperature for 48 hours, after which 200 ml of water are added to the solution and the organic phase is separated off. The remaining aqueous phase is extracted with methylene chloride and the collected organic phases are washed with water. Drying over sodium sulfate and evaporation of the organic phase give 87.4 g (90%) of cis-1-(4-fluorophenyl)-2-(2-chlorophenyl)-cyclopropyl cyanide of melting point 108°–115° C.

EXAMPLE C 32.1 g of cis-1-(4-fluorophenyl)-2-(2-chlorophenyl)-cyclopropyl cyanide are taken up in 250 ml of toluene, and 100 ml of diisobutylaluminum hydride (1.2 molar in toluene) are added dropwise at from 0° to 4° C. under a nitrogen atmosphere. The reaction solution is stirred for one hour at room temperature, after which 500 ml of 5% strength sulfuric acid are added rapidly to it and the mixture is extracted several times with methyl tert-butyl ether. The organic phase is washed twice with water, dried over sodium sulfate and evaporated down. 28.2 g (89%) of cis-1-(4-fluorophenyl)-2-(2-chlorophenyl)-cyclopropylcarbaldehyde of melting point 79°–80° C. are obtained.

EXAMPLE D 26.6 g of cis-1-(4-fluorophenyl)-2-(2-chlorophenyl)-cyclopropylcarbaldehyde are dissolved in 100 ml of ethanol, and 1.22 g of sodium borohydride are added at room temperature. The solvent is then evaporated off under reduced pressure, the residue is taken up in methylene chloride, and the solution is washed with water, dried over sodium sulfate and evaporated down. Recrystallization of the residue from toluene gives 26.4 g (98%) of cis-1-hydroxymethyl-1-(4-fluorophenyl)-2-(2-chlorophenyl)-cyclopropane of melting point 86°–89° C.

EXAMPLE E 22.7 g of 4-methylbenzenesulfonyl chloride are added to a solution of 26.4 g of cis-1-hydroxymethyl-1-(4-fluorophenyl)-2-(2-chlorophenyl)-cyclopropane in 150 ml of methylene chloride at room temperature. After 24 hours, the reaction mixture is washed with aqueous sodium bicarbonate solution and water, dried over sodium sulfate and evaporated down under reduced pressure. The residue gives 40.2 g (98%) of cis-1-(4-methylphenylsulfonyloxymethyl)-1-(4-fluorophenyl)-2-(2-chlorophenyl)-cyclopropane, which is then further processed with triazole. II Preparation of the end products

EXAMPLE 1

4.8 g of sodium hydroxide are added to a solution of 6.9 g of 1,2,4-triazole in 100 ml of N-methylpyrrolidone and the mixture is heated at 50° C. for 30 minutes. After the reaction mixture has been cooled to room temperature, 21.5 g of cis-1-(4-methylphenylsulfonyloxymethyl)-1-(4-fluorophenyl)-2-(2-chlorophenyl)-cyclopropane, which has been dissolved in 50 ml of N-methylpyrrolidone, are slowly added dropwise to the solution and the mixture is stirred for 12 hours at room temperature. Thereafter, 200 ml of water are added and the mixture is extracted several times with methyl tert-butyl ether, and the organic phase is washed twice with water, dried over sodium sulfate and evaporated down. The remaining residue is chromatographed over silica gel using 9:1 n-hexane/ethyl acetate, 12 g (76%) of cis-1-(1,2,4-triazol-1-ylmethyl)-1-(4-fluorophenyl)-2-(2-chlorophenyl)-cyclopropane of melting point 97°-101° C. being obtained (compound no. 1).

EXAMPLE 2

6.8 g of thionyl chloride are added to a solution of 15.8 g of 1,2,4-triazole in 100 ml of methylene chloride at 0° C. under a nitrogen atmosphere. After the end of the addition, the mixture is stirred for 30 minutes at room temperature and 10 g of cis-1-(4-fluorophenyl)-2-(2-fluorophenyl)-cyclopropylcarbaldehyde are then added. The reaction mixture is stirred for from 12 to 15 hours at room temperature, after which 100 ml of water are added to the solution and the organic phase is separated off. The remaining aqueous phase is extracted twice by shaking with methylene chloride, and the collected organic phases are washed twice with saturated sodium bicarbonate solution. The isolated phase is then dried over sodium sulfate and evaporated down, and the remaining residue is chromatographed over silica gel using 9:1 n-hexane/ethyl acetate. 3.9 g (28%) of cis-1-(1,2,4-triazol-1-ylchloromethyl)-1-(4-fluorophenyl)-2-(2-fluorophenyl)-cyclopropane are obtained as a 2:1 diastereomer mixture (compound no. 20).

The compounds shown in the Table can be prepared similarly to Examples 1 and 2.

TABLE

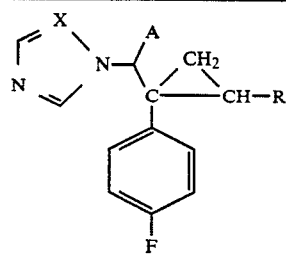

| Ex. no. | R | A | X | m.p./IR | Isomer |
|---|---|---|---|---|---|
| 1 | 2-Cl—C$_6$H$_4$ | H | N | 97–101° C. | cis |
| 2 | 2-Cl—C$_6$H$_4$ | H | CH | 230° C. | cis |
| 3 | 2-Cl—C$_6$H$_4$ | F | N | | |
| 4 | 2-Cl—C$_6$H$_4$ | Cl | N | 144–148° C. | enantiomer mixture |
| 5 | 2-Cl—C$_6$H$_4$ | Cl | CH | 105–110° C. | D1:D2 = 3:1 |
| 6 | 2-Cl—C$_6$H$_4$ | Br | N | | |
| 7 | 2-Cl—C$_6$H$_4$ | Br | CH | | |
| 8 | 3-Cl—C$_6$H$_4$ | H | N | | |
| 9 | 3-Cl—C$_6$H$_4$ | H | CH | | |
| 10 | 3-Cl—C$_6$H$_4$ | Cl | N | | |
| 11 | 4-Cl—C$_6$H$_4$ | H | N | | |
| 12 | 4-Cl—C$_6$H$_4$ | H | CH | | |
| 13 | 4-Cl—C$_6$H$_4$ | Cl | N | | |
| 14 | 4-Cl—C$_6$H$_4$ | Cl | CH | | |
| 15 | 4-Cl—C$_6$H$_4$ | Br | N | | |
| 16 | 4-Cl—C$_6$H$_4$ | Br | CH | | |
| 17 | 2-F—C$_6$H$_4$ | H | N | | |
| 18 | 2-F—C$_6$H$_4$ | H | CH | | |
| 19 | 2-F—C$_6$H$_4$ | F | N | | |
| 20 | 2-F—C$_6$H$_4$ | Cl | N | 1513, 1496, 1236, 840, 819, 760 cm$^{-1}$ | D1:D2 = 2:1 |
| 21 | 2-F—C$_6$H$_4$ | Cl | CH | | |
| 22 | 4-F—C$_6$H$_4$ | H | N | | |
| 23 | 4-F—C$_6$H$_4$ | H | CH | | |
| 24 | 4-F—C$_6$H$_4$ | F | N | | |
| 25 | 4-F—C$_6$H$_4$ | Cl | N | | |
| 26 | 4-F—C$_6$H$_6$ | Br | N | | |
| 27 | 2,4-F$_2$—C$_6$H$_3$ | H | N | | |
| 28 | 2,4-F$_2$—C$_6$H$_3$ | Cl | N | | |
| 29 | 2,4-F$_2$—C$_6$H$_3$ | F | N | | |
| 30 | 2-Cl-4-F—C$_6$H$_3$ | H | N | | |
| 31 | 2-Cl-4-F—C$_6$H$_3$ | H | CH | | |
| 32 | 2-Cl-4-F—C$_6$H$_3$ | F | N | | |
| 33 | 2-Cl-4-F—C$_6$H$_3$ | Cl | N | | |
| 34 | 2-Cl-4-F—C$_6$H$_3$ | Br | N | | |
| 35 | 2-CF$_3$—C$_6$H$_4$ | H | N | 1514, 1315, 1162, 1121, 839, 769 cm$^{-1}$ | cis |
| 36 | 2-CF$_3$—C$_6$H$_4$ | H | CH | 1513, 1315, 1162, 1121, 838, 769 cm$^{-1}$ | cis |
| 37 | 2-CF$_3$—C$_6$H$_4$ | F | N | | |
| 38 | 2-CF$_3$—C$_6$H$_4$ | Cl | N | | |
| 39 | 2-CF$_3$—C$_6$H$_4$ | Br | N | | |
| 40 | 3-CF$_3$—C$_6$H$_4$ | H | N | | |
| 41 | 4-CF$_3$—C$_6$H$_4$ | H | N | | |
| 42 | 4-CF$_3$—C$_6$H$_4$ | Cl | N | | |
| 43 | 2-OCH$_3$—C$_6$H$_4$ | H | N | | |
| 44 | 2-OCH$_3$—C$_6$H$_4$ | H | CH | | |
| 45 | 2-OCH$_3$—C$_6$H$_4$ | Cl | N | | |
| 46 | 3-OCH$_3$—C$_6$H$_4$ | H | N | | |

TABLE-continued

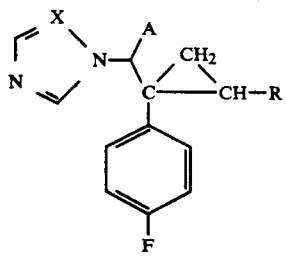

| Ex. no. | R | A | X | m.p./IR | Isomer |
|---|---|---|---|---|---|
| 47 | 4-OCH$_3$—C$_6$H$_4$ | H | N | | |
| 48 | 4-OCH$_3$—C$_6$H$_4$ | H | CH | | |
| 49 | 2,3-Cl$_2$—C$_6$H$_3$ | H | N | | |
| 50 | 2,5-Cl$_2$—C$_6$H$_3$ | H | N | | |
| 51 | 2,6-Cl$_2$—C$_6$H$_3$ | H | N | | |
| 52 | 2-Br—C$_6$H$_4$ | H | N | | |
| 53 | 3-Br—C$_6$H$_4$ | H | N | | |
| 54 | 4-Br—C$_6$H$_4$ | H | N | | |
| 55 | 3-NO$_2$—C$_6$H$_4$ | H | N | | |
| 56 | 3-NO$_2$—C$_6$H$_4$ | Cl | N | | |
| 57 | 4-NO$_2$—C$_6$H$_4$ | H | N | | |
| 58 | 2,4-OCH$_3$—C$_6$H$_3$ | H | N | | |
| 59 | 2,4-OCH$_3$—C$_6$H$_3$ | H | N | | |
| 60 | 4-C$_2$H$_5$—C$_6$H$_4$ | H | N | | |
| 61 | 4-O-tert.-butyl-C$_6$H$_4$ | H | N | | |
| 62 | 4-O-phenyl-C$_6$H$_4$ | H | N | | |
| 63 | 3-pyridyl | H | N | | |
| 64 | cyclopropyl | H | N | | |
| 65 | cyclopentyl | H | N | | |
| 66 | cyclopentyl | H | CH | | |
| 67 | cyclopentyl | Cl | N | | |
| 68 | cyclohexyl | H | N | | |
| 69 | cyclohexyl | H | CH | | |
| 70 | cyclohexyl | F | N | | |
| 71 | cyclohexyl | Cl | N | | |
| 72 | cyclohexyl | Cl | CH | | |
| 73 | cyclohexyl | Br | N | | |
| 74 | 3-cyclohexenyl | H | N | | |
| 75 | norbornyl | H | N | | |
| 76 | 4-tetrahydropyranyl | H | N | | |
| 77 | C$_6$H$_5$ | H | N | | |
| 78 | C$_6$H$_5$ | H | CH | | |
| 79 | C$_6$H$_5$ | Cl | N | | |
| 80 | C$_6$H$_5$ | Cl | CH | | |
| 81 | C$_6$H$_5$ | F | N | | |
| 82 | CH$_3$ | H | N | | |
| 83 | C$_2$H$_5$ | H | N | | |
| 84 | tert.-C$_4$H$_9$ | H | N | | |
| 85 | tert.-C$_4$H$_9$ | H | CH | | |
| 86 | tert.-C$_4$H$_9$ | Cl | N | | |
| 87 | C$_{10}$H$_7$ | H | N | | |
| 88 | C$_{10}$H$_7$ | H | CH | | |
| 89 | C$_{12}$H$_9$ | H | N | | |
| 90 | C$_{12}$H$_9$ | H | CH | | |

D1:D2 = ratio of the diastereomers produced

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants, Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel compounds may exercise a variety of influences on practically all plant development stages, and are therefore used as growth regulators. The diversity of action of growth regulators depends especially on
(a) the type and variety of plant;
(b) the time applied, with reference to the development stage of the plants and the time of the year;
(c) the place and method of application (seed treatment, soil treatment, or application to foliage);
(d) climatic factors, e.g., average temperature, amount of precipitate, sunshine and duration;
(e) soil conditions (including fertilization);
(f) the formulation of the active ingredient; and
(g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker. Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The compounds of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a disinfectant), but also to the soil, i.e., via the roots, and—the method particularly preferred—to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.01 to 10, g are generally required.

For foliage and soil treatment, amounts of from 0.01 to 10, and preferably from 0.02 to 3, kg/ha are generally considered to be sufficient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 35 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 2 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 36 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1 is well mixed with 3 parts by weight of the sodium salt of diisobutylnapthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 35 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 36 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 1 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichlormethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide, 8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, the compounds 1-(1,2,4-triazol-1-ylmethyl)-1-(4-chlorophenyl)-2-(2-chlorophenyl)-cyclopropane (A) and 1-(1,2,4-triazol-1-ylmethyl)-1-(4-fluorophenyl)-2-(2,4-dichlorophenyl)-cyclopropane (B) disclosed in EP No. 121,081 were used.

USE EXAMPLE 1

Action on wheat brown rust

Leaves of pot-grown wheat seedlings of the "Kanzler" variety were dusted with spores of brown rust (Puccinia recondita). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 1 and 35, applied as 0.0015 wt % spray liquors, had a better fungicidal action (100%) than prior art comparative agents A and B (90%).

USE EXAMPLE 2

Action on Plasmopara viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 2 and 36, applied as 0.0125% spray liquors, had a better fungicidal action (90%) than prior art comparative agent B (20%).

USE EXAMPLE 3

Action on Helminthosporium teres (Pyrenophora teres)

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus Pyrenophora teres, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredients 1, 35 and 36, applied as 0.0125% spray liquors, had a very good fungicidal action (100%).

To determine the growth-regulating properties of the candidate compounds, the test plants were grown in plastic pots (approx. 12.5 cm in diameter) in a substrate provided with sufficient nutrients.

In the preemergence treatment method, the candidate compounds were sprayed as aqueous formulations onto the seedbed on the day of sowing.

In the postemergence method, the compounds were sprayed as aqueous formulations onto the plants. The growth-regulating action observed was confirmed at the end of the experiment by measuring the height of the plants. The figures obtained were compared with the growth height of the untreated plants. The prior art active ingredient chlorocholine chloride (C) was used for comparison purposes.

The reduction in growth height was also accompanied by a deeper leaf coloration. The increased chlorophyll content is indicative of an increased rate of photosynthesis, making for bigger yields.

The individual data are given in the following tables.

COMPARATIVE AGENT:

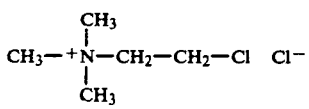  C

USE EXAMPLE 4

Spring barley, "Aramir" variety Preemergence (soil) treatment

| Active ingredient no. | Concentration mg of a.i./vessel | Growth height relative |
|---|---|---|
| untreated | — | 100 |
| C | 6 | 100 |
| 1 | 6 | 67.8 |
| 35 | 6 | 60.2 |

USE EXAMPLE 5

Sunflowers, "Sorex" variety
Postemergence treatment

| Active ingredient no. | Concentration mg of a.i./vessel | Growth height relative |
|---|---|---|
| untreated | — | 100 |
| C | 6 | 100 |
| 35 | 6 | 90.3 |

USE EXAMPLE 6

Lawn
Leaf treatment

| Active ingredient no. | Concentration mg of a.i./vessel | Growth height relative |
|---|---|---|
| untreated | — | 100 |
| C | 1.5 | 100.8 |
|  | 6 | 94.5 |
| 1 | 1.5 | 75.6 |
|  | 6 | 25.2 |
| 35 | 1.5 | 88.2 |
|  | 6 | 25.2 |

We claim:

1. An azolylmethylcyclopropane of the formula:

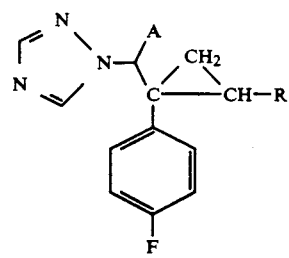

wherein R is a $C_3$-$C_8$-cycloalkyl, $C_5$-$C_8$-cycloalkenyl, tetrahydropyranyl or norbornyl group or said R group monosubstituted, disubstituted or trisubstituted by halogen, nitro, phenoxy, amino, $C_{1-4}$ alkyl, $C_{1-4}$ alkoxy or $C_{1-4}$ haloalkyl, A is H, F, Cl or Br and their plant-tolerated acid addition salts and metal complexes.

2. The azolylmethylcyclopropane of claim 1, wherein R is $C_{3-8}$ cycloalkyl.

3. The azolylmethylcyclopropane of claim 1, wherein R is $C_{5-8}$ cycloalkenyl.

4. The azolylmethylcyclopropane of claim 1, wherein R is tetrahydropyranyl.

5. The azolylmethylcyclopropane of claim 1, wherein R is norbornyl.

6. An azolylmethylcyclopropane of the formula:

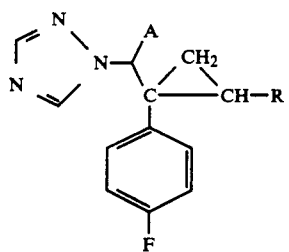

wherein R is a phenyl group monosubstituted with halogen or trifluoromethyl in the ortho-position, A is H and their plant-tolerated acid addition salts and metal complexes.

7. The azolylmethylcyclopropane of claim 6, wherein R is an ortho-chloro-phenyl group.

8. The azolylmethylcyclopropane of claim 6, wherein R is an ortho-trifluoromethyl-phenyl group.

9. A fungicidal composition containing a carrier and a fungicidal amount of an azolylmethylcyclopropane of the formula I as set forth in claim 1, or a plant-tolerated acid addition salt or metal complex thereof.

10. A growth-regulating composition containing a carrier and a growth-regulating amount of an azolylmethylcyclopropane of the formula I as set forth in claim 1 or a plant-tolerated acid addition salt or metal complex thereof.

11. A fungicidal composition containing a carrier and a fungicidal amount of the azolylmethylcyclopropane of claim 6.

12. A growth-regulating composition containing a carrier and a growth-regulating amount of the azolylmethylcyclopropane of claim 6.

13. A process for regulating plant growth, wherein the plants, the soil or the seed are treated with a growth-regulating amount of an azolylmethlcyclopropane of the formula I as set forth in claim 1, or a plant-tolerated acid addition salt or metal complex thereof.

14. A process for combating fungi, comprising contacting fungi with a fungicidally effective amount of the azolylmethylcyclopropane of claim 6 or a plant-tolerated acid addition salt or metal complex thereof.

15. A process for regulating plant growth, wherein the plants, the soil or the seed are treated with a growth-regulating amount of the azolylmethylcyclopropane of claim 6 or a plant-tolerated acid addition salt or metal complex thereof.

16. A process for combating fungi, comprising contacting fungi with a fungicidally effective amount of the azolylmethylcyclopropane of claim 1 or a plant-tolerated acid addition salt or metal complex thereof.

* * * * *